(12) United States Patent
Maguire

(10) Patent No.: US 10,117,848 B2
(45) Date of Patent: Nov. 6, 2018

(54) HIGHLY WATER-SOLUBLE SALTS OF A SHORT ACTING PHENYLALKYLAMINE CALCIUM CHANNEL BLOCKER AND USES THEREOF

(71) Applicant: Milestone Pharmaceuticals Inc., Saint-Laurent (CA)

(72) Inventor: Martin P. Maguire, Westmount (CA)

(73) Assignee: Milestone Pharmaceuticals Inc., Saint-Laurent, QC (CA)

( * ) Notice: Subject to any disclaimer, the term of this patent is extended or adjusted under 35 U.S.C. 154(b) by 0 days.

(21) Appl. No.: 15/566,122

(22) PCT Filed: Apr. 13, 2016

(86) PCT No.: PCT/CA2016/050425
§ 371 (c)(1),
(2) Date: Oct. 12, 2017

(87) PCT Pub. No.: WO2016/165014
PCT Pub. Date: Oct. 20, 2016

(65) Prior Publication Data
US 2018/0110752 A1   Apr. 26, 2018

Related U.S. Application Data

(60) Provisional application No. 62/147,427, filed on Apr. 14, 2015.

(51) Int. Cl.
| | |
|---|---|
| *A61K 31/277* | (2006.01) |
| *A61P 9/06* | (2006.01) |
| *A61K 47/10* | (2017.01) |
| *A61K 47/26* | (2006.01) |
| *A61P 9/10* | (2006.01) |
| *A61K 47/02* | (2006.01) |
| *A61P 25/06* | (2006.01) |
| *A61K 47/20* | (2006.01) |
| *A61K 47/18* | (2017.01) |
| *A61K 9/00* | (2006.01) |
| *A61K 47/12* | (2006.01) |
| *C07C 255/42* | (2006.01) |
| *A61K 9/08* | (2006.01) |

(52) U.S. Cl.
CPC .......... *A61K 31/277* (2013.01); *A61K 9/0043* (2013.01); *A61K 9/08* (2013.01); *A61K 47/02* (2013.01); *A61K 47/10* (2013.01); *A61K 47/12* (2013.01); *A61K 47/183* (2013.01); *A61K 47/20* (2013.01); *A61K 47/26* (2013.01); *A61P 9/06* (2018.01); *A61P 9/10* (2018.01); *A61P 25/06* (2018.01); *C07C 255/42* (2013.01)

(58) Field of Classification Search
None
See application file for complete search history.

(56) References Cited

U.S. PATENT DOCUMENTS

| | | | |
|---|---|---|---|
| 9,227,918 B2 | 1/2016 | Maguire et al. | |
| 9,463,179 B2 | 10/2016 | Maguire et al. | |
| 9,737,503 B2 | 8/2017 | Maguire et al. | |
| 10,010,522 B2 | 7/2018 | Maguire et al. | |
| 10,010,523 B2 | 7/2018 | Maguire et al. | |
| 10,010,524 B2 | 7/2018 | Maguire et al. | |
| 2005/0191245 A1 | 9/2005 | Adams et al. | |
| 2009/0318413 A1 | 12/2009 | Berger et al. | |
| 2017/0312241 A1* | 11/2017 | Maguire | ............... A61K 31/277 |
| 2017/0312242 A1* | 11/2017 | Maguire | ............... C07C 255/43 |

FOREIGN PATENT DOCUMENTS

| | | |
|---|---|---|
| CA | 2693627 A1 | 12/2008 |
| WO | WO-2008/156820 A1 | 12/2008 |

OTHER PUBLICATIONS

Abdel et al., "Bioavailability enhancement of verapamil HCl via intranasal chitosan microspheres," Eur J Pharm Sci. 51:59-66 (2014).
Arnold et al., "Pharmacodynamics of acute intranasal administration of verapamil: comparison with i.v. and oral administration," Biopharmaceutics and Drug Disposition. 6(4):447-54 (1985).
International Preliminary Report on Patentability for International Application No. PCT/CA2016/050425, dated Oct. 17, 2017 (8 pages).
International Search Report for International Application No. PCT/CA2016/050425, dated Jul. 11, 2016 (5 pages).
Written Opinion of the International Searching Authority for International Application No. PCT/CA2016/050425, dated Jul. 11, 2016 (7 pages).
Yenil et al., "Preparation and evaluation of bioadhesive inserts containing verapamil hydrochloride for nasal delivery," Lat Am J Pharm. 32(8):1170-7 (2013).

* cited by examiner

*Primary Examiner* — Brian J Davis
(74) *Attorney, Agent, or Firm* — Clark & Elbing LLP

(57) ABSTRACT

The present invention includes surprisingly water-soluble salts of a phenylalkylamine compound that are potent antagonists of L-type calcium channels. Aqueous solutions including salts of the instant invention are formulated for nasal administration and provide a novel therapeutic platform for the treatment of stable angina, migraine, and cardiac arrhythmia, such as paroxysmal supraventricular tachycardia.

39 Claims, No Drawings

HIGHLY WATER-SOLUBLE SALTS OF A SHORT ACTING PHENYLALKYLAMINE CALCIUM CHANNEL BLOCKER AND USES THEREOF

BACKGROUND OF THE INVENTION

The invention relates to salts including a phenylalkylamine compound that exhibit surprisingly high solubility in aqueous solution. The salts of the instant invention are validated antagonists of L-type calcium channels and provide a new therapeutic platform for the treatment of cardiac arrhythmias, such as paroxysmal supraventricular tachycardia, stable angina, and migraines.

Cardiac Arrhythmia

Cardiac arrhythmia, or abnormal heart rhythm, is caused by abnormal excitation and conduction to the heart. A normal heartbeat is regulated by the sinoatrial (SA) node, a collection of cells embedded within the right atrium proximal to the superior vena cava. Under healthy physiological conditions, the SA node spontaneously initiates action potentials at regular intervals and propagates these electrochemical signals from the right atrium to the left atrium. Each coordinated pulse induces an influx of calcium ions ($Ca^{2+}$) into the cardiomyocyte fibers of the SA node through voltage-gated calcium channels, which ultimately enables the cardiac muscle tissue to contract and expel blood from the atria into the ventricles. This signal is subsequently propagated to the atrioventricular (AV) node, which propagates the action potential to the right and left ventricles. This signal triggers an influx of extracellular calcium, which in turn facilitates contraction of ventricular cardiomyocytes and the expulsion of blood from the heart and into circulation.

The precise coordination of these events is vital to maintaining a regular heartbeat, and the aberrant activity of this electrochemical conduction system gives rise to arrhythmia. A recurrent arrhythmia with an abrupt onset and termination is designated as paroxysmal. Symptoms of paroxysmal supraventricular tachycardia (PSVT) include episodes of regular and paroxysmal palpitations with sudden onset and termination (Blomstrom-Lundqvist et al., *J. Am. Coll. Cardiol.*, 2003, 42:1493-531). The signaling mechanisms that underlie PSVT include the initiation and propagation of action potentials along accessory nodes that cause abnormal cardiomyocyte contractions that interfere with the coordinated atrial-to-ventricular blood flow. The most common form of PSVT is AV nodal reentrant tachycardia (AVNRT), a disorder characterized by the development of conducting tissue proximal to the AV node. This tissue forms a closed loop known as a reentry circuit, which enables action potentials to be propagated circularly throughout the heart rather than in a linear fashion. As a result, patients experience rapid palpitations and severely elevated heart rates. Episodes of tachycardia are often accompanied by a drop in blood pressure, which can induce dizziness or fainting. It is estimated that PSVT affects greater than 1.7 million treatable patients in the United States, and over 89,000 new cases are reported annually. Strikingly, many of these patients do not exhibit other signs of cardiovascular disease. Episodes of PSVT can be induced by various factors, including physical and psychological stress, infection, anemia, menstruation, and pregnancy (Lee, et al., *Curr. Probl. Cardiol.*, 2008, 33:467-546).

Current Modes of Treatment

There are currently several therapeutic modalities available to PSVT patients. However, these platforms generally suffer from several deficiencies, chief among them being invasiveness or inefficiency. Patients can frequent the emergency room for immediate intervention during an episode, but this strategy provides only temporary relief. Such patients may continue to experience episodes of tachycardia throughout their lifetimes. Patients who suffer from chronic episodes of PSVT can have the nodal fibers that propagate anomalous action potentials ablated in order to permanently disrupt the mechanism that underlies the irregular cardiomyocyte contractions. This procedure typically requires that a catheter tube be inserted into the patient's throat in order to access the heart, where a low-voltage pulse of electricity is delivered to the aberrant signaling tissue. This process is highly invasive, and patients are often fearful of undergoing this form of treatment.

Alternatively, patients who suffer from chronic PSVT can take oral medication to help attenuate the severity or reduce the frequency of arrhythmia episodes. Calcium channel blockers represent a class of compounds that is functionally well-suited to ameliorate the symptoms of tachycardia, as these compounds are capable of reducing the influx of extracellular calcium into cardiomyocytes that ultimately leads to muscle contraction. Prevalent examples of calcium channel antagonists include verapamil and diltiazem, both of which are potent inhibitors of calcium influx and are widely used to treat PSVT. However, despite the widespread use of these therapeutics, patients who take these medications may continue to experience episodes of tachycardia.

There currently is no commercially available therapeutic product that can be self-administered during an episode of PSVT in order to alleviate the symptoms during the episode. While calcium channel blockers provide a validated strategy for terminating such episodes, the development of such a product is a challenge due to the precise pharmacokinetic profile necessary to rapidly alleviate the symptoms without potentiating off target-mediated toxicity. A desirable therapeutic must have the capacity for rapid infusion into the bloodstream of a patient in a therapeutically effective quantity and thus promptly terminate an episode of PSVT. The drug must be subsequently metabolized and inactivated in rapid fashion for a normal resting heart rate to be established. Current calcium channel blocker formulations are designed for oral administration. The passage of these compounds into the gastrointestinal tract and the ensuing metabolism that occurs hinders the rapid entry of these drugs into the bloodstream and renders the ideal pharmacokinetic profile inaccessible. Instead, these drugs are released on a slower time scale via absorption through the intestinal epithelium, which delays their access to faulty cardiac muscle tissue.

The invention disclosed herein provides an innovative strategy for treating cardiac arrhythmias, such as PSVT. The instant invention includes a novel formulation of a calcium channel blocker that enables the rapid delivery of the active compound into the bloodstream so as to reach maximum concentrations in plasma of PSVT patients within minutes of administration. This facilitates the rapid termination of PSVT episodes. The formulation provides an additional benefit in that the active calcium channel blocker is subsequently metabolized and inactivated rapidly after reaching maximal plasma concentrations. This pharmacokinetic profile is ideal for a drug that can treat PSVT immediately during an episode. The formulation of the present invention thus represents a new therapeutic paradigm for targeting faulty cardiac signaling in a precise and rapid fashion.

SUMMARY OF THE INVENTION

The present invention relates to the use of an aqueous solution that contains a pharmaceutically effective amount of a salt of a calcium channel antagonist for use in treating stable angina, migraine, and cardiac arrhythmia, such as PSVT. The salts of the instant invention are formulated for nasal administration, which represents an administration route that has not previously been exploited for treating PSVT. One of the challenges associated with nasal administration is the volumetric limit imposed by the nasal cavity. Administration of nasal sprays is typically limited to approximately 150 to 200 μL, beyond which point the liquid solution begins to enter the throat. This, in turn, imposes a limit on the quantity of a pharmaceutically active agent that can be delivered to the epithelial lining of the nasal cavity. The salts of the instant invention exhibit a surprisingly high solubility in aqueous solution, which enables the development of concentrated liquid solutions that can deliver therapeutically effective quantities of the active agent to the nasal epithelium. Nasal administration of the active agent is beneficial for achieving an ideal pharmacokinetic profile, as the ability of the therapeutic compound to traverse the nasal mucosa and rapidly enter the bloodstream renders the drug capable of quickly targeting faulty signaling in muscle tissue. The novel formulations described herein represent a new therapeutic regimen for alleviating the symptoms of stable angina, migraine, and cardiac arrhythmia, such as PSVT, during an episode.

Embodiments of the invention include an aqueous composition formulated for nasal administration containing a pharmaceutically acceptable salt or free base of a compound selected from the group consisting of a compound of the formula (I)

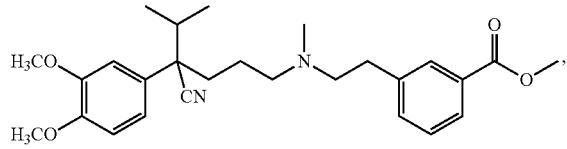

verapamil (2-(3,4-dimethoxyphenyl)-5-[2-(3,4-dimethoxyphenyl)ethyl-methylamino]-2-propan-2-ylpentanenitrile), represented by the formula

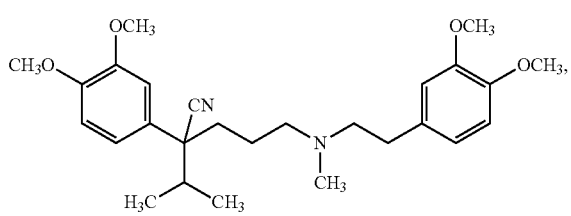

gallopamil (5-[2-(3,4-dimethoxyphenyl)ethyl-methylamino]-2-propan-2-yl-2-(3,4,5-trimethoxyphenyl)pentanenitrile), represented by the formula

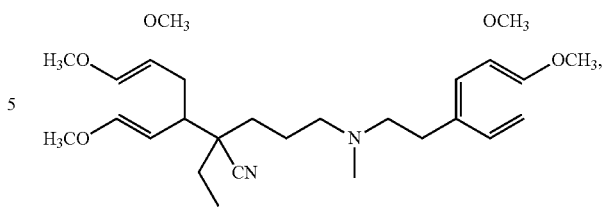

and devapamil (2-(3,4-Dimethoxyphenyl)-2-isopropyl-5-((m-methoxyphenethyl)methylamino)valeronitrile), represented by the formula

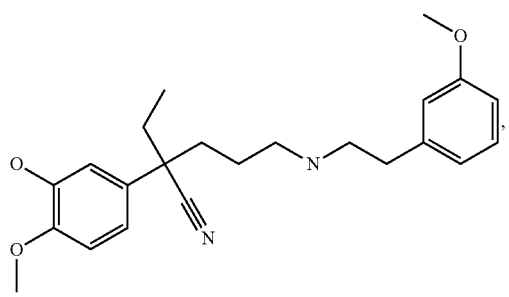 [SMILES: CCC(C#N)(CCCNCCc1cccc(OC)c1)c1ccc(OC)c(O)c1]

or a racemate or enantiomer thereof, wherein the compound is dissolved in the aqueous composition at a concentration of between 150 mg/mL and 600 mg/mL.

In certain embodiments, the compound that is dissolved in the aqueous composition is compound I. In preferred embodiments, the compound that is dissolved in the aqueous composition is the S-enantiomer of compound I.

Embodiments of the present invention include an aqueous composition formulated for nasal administration containing a pharmaceutically acceptable salt or free base of a compound selected from the group consisting of

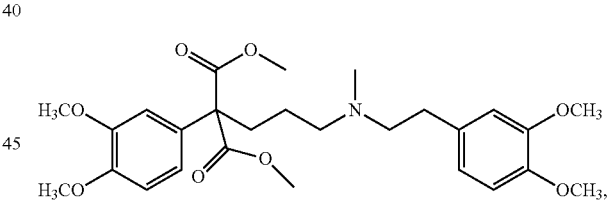

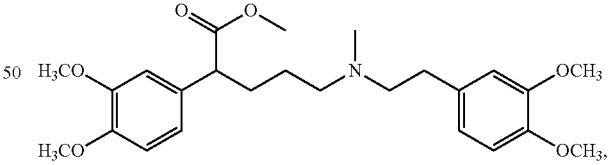

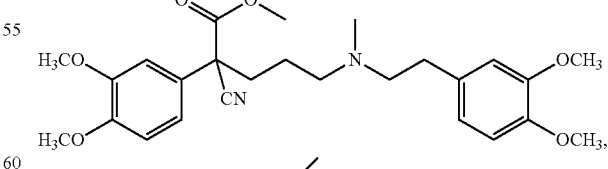

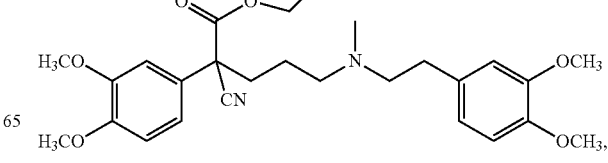

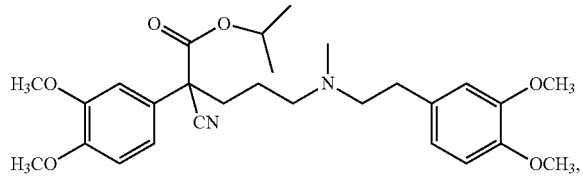
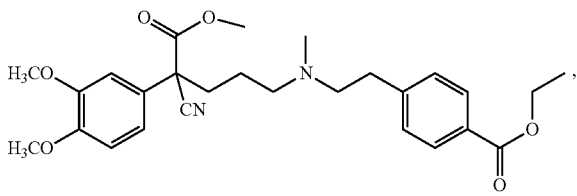

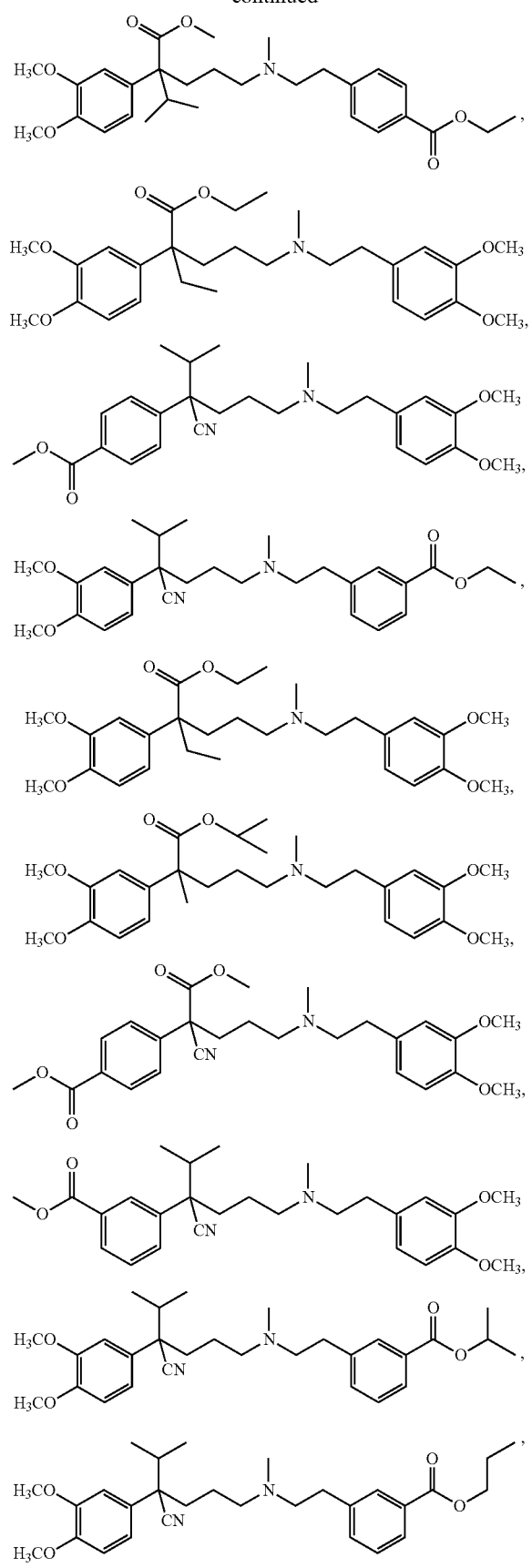
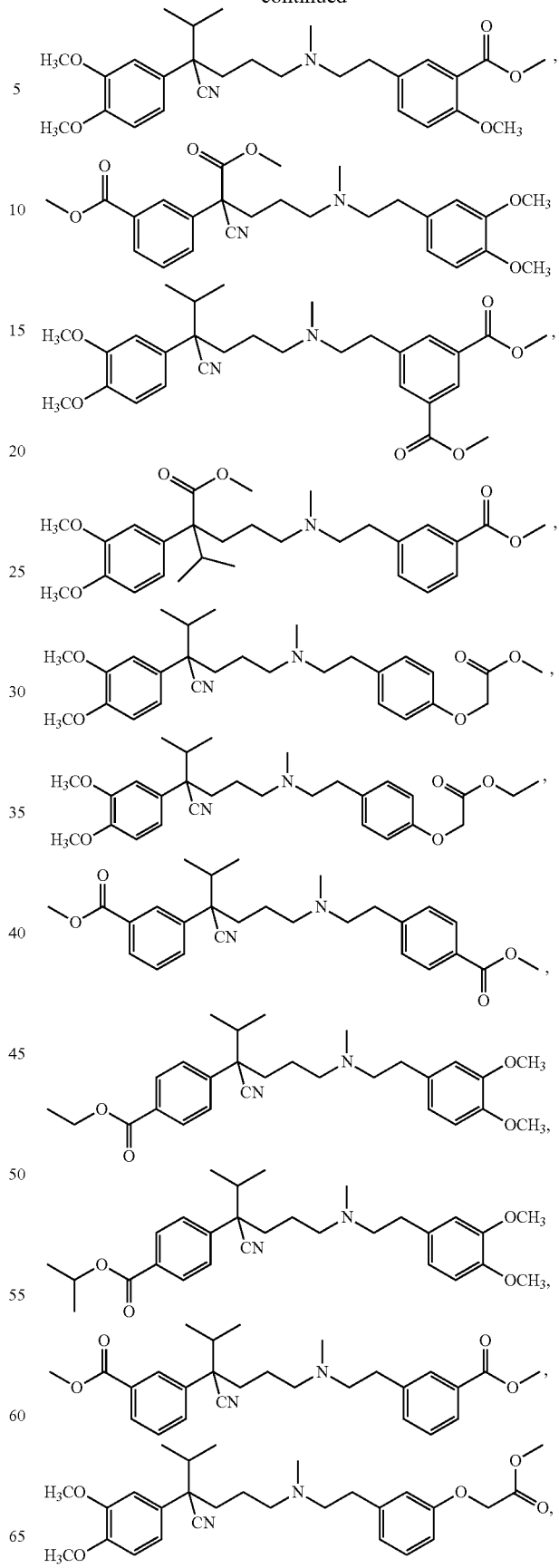

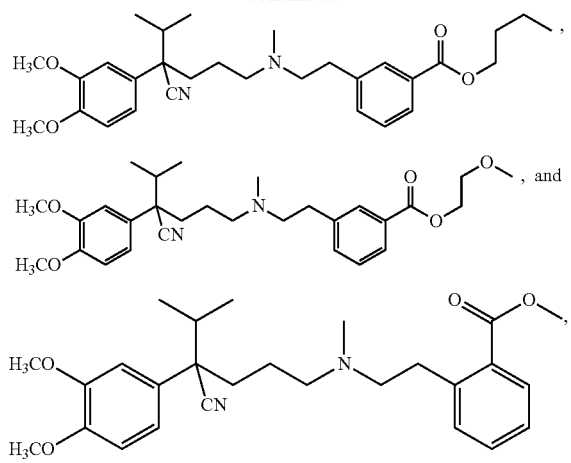

or a racemate or enantiomer thereof, wherein the compound is dissolved in the aqueous composition at a concentration of between 150 mg/mL and 600 mg/mL.

Embodiments of the present invention also include an aqueous composition formulated for nasal administration containing a pharmaceutically acceptable salt or free base of a compound selected from the group consisting of

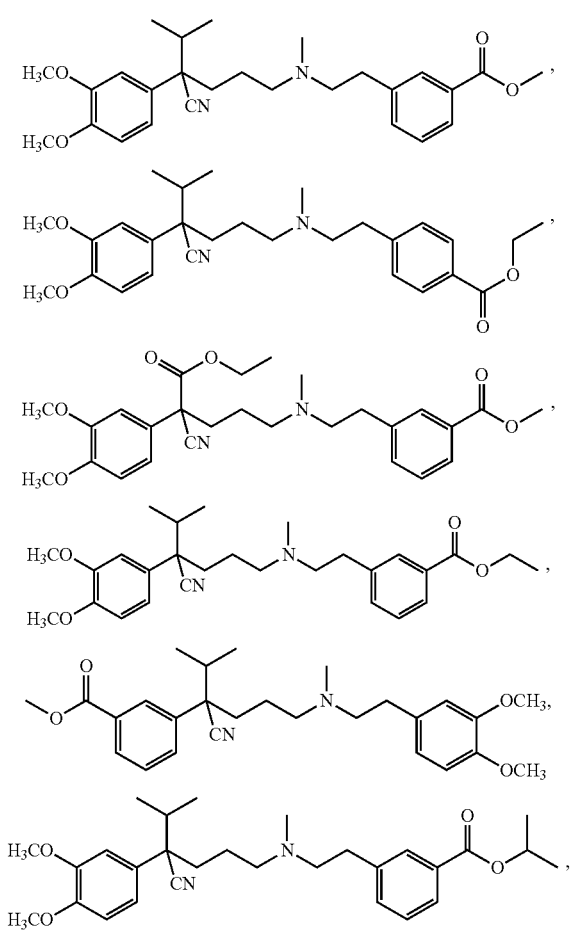

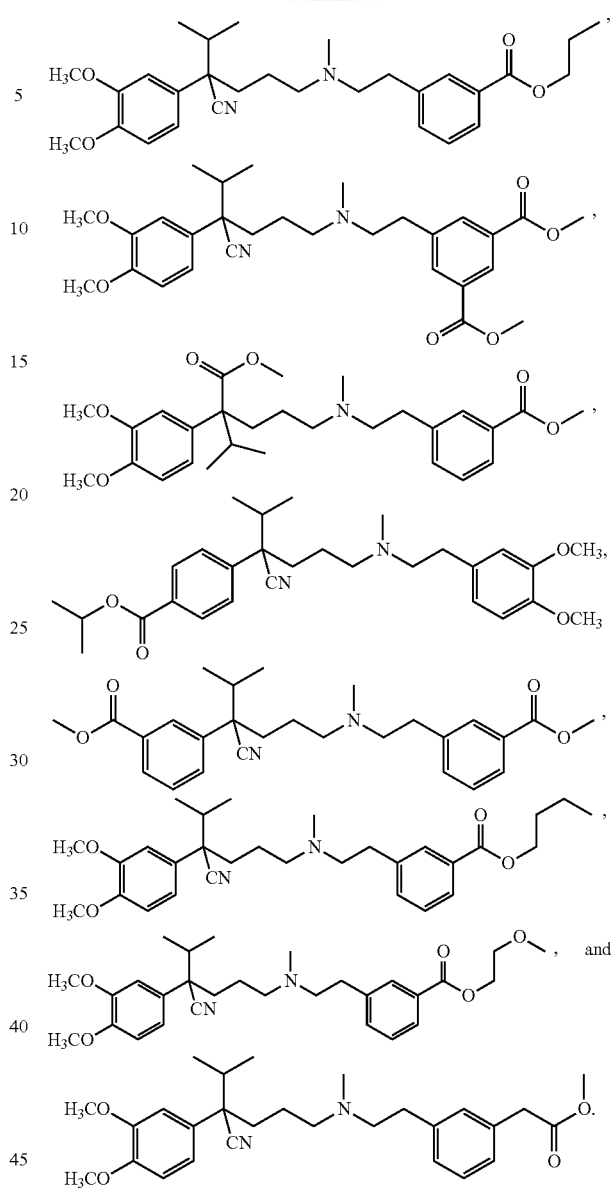

or a racemate or enantiomer thereof, wherein the compound is dissolved in the aqueous composition at a concentration of between 150 mg/mL and 600 mg/mL.

In particular embodiments, the concentration of the compound that is dissolved in the aqueous solution is approximately 350 mg/mL. In alternative embodiments, the concentration of the compound that is dissolved in the aqueous solution is approximately 450 mg/mL. In certain cases, the aqueous composition of the instant invention includes from 40% to 85% (w/v) water. In additional embodiments of the invention, the aqueous composition has a pH of 4.5±1.5.

Embodiments of the present invention include the aqueous composition of any of the above embodiments, wherein the aqueous composition contains a compound described herein, e.g., compound I, verapamil, gallopamil, or devapamil and between 0.5 and 1.5 molar equivalents of acetic acid relative to the compound. Alternative embodiments of the present invention include the aqueous composition of any of the above embodiments, wherein the aqueous composition contains a compound described herein, e.g., compound I, verapamil, gallopamil, or devapamil and between 0.5 and 1.5 molar equivalents of methanesulfonic acid relative to the compound.

In certain cases, the invention includes the composition of any of the above embodiments, wherein the composition contains a chelating agent. In certain embodiments, the chelating agent is an aminopolycarboxylic acid.

Additional embodiments of the invention include the composition of any of the above embodiments, wherein the aqueous composition contains ethylenediaminetetracetic acid (EDTA).

In other embodiments of the instant invention, the composition of any of the above embodiments includes a pH adjusting agent selected from the group consisting of sulfuric acid and methanesulfonic acid. In preferred embodiments, the pH adjusting agent is sulfuric acid.

Additional embodiments of the invention include the composition of any of the above embodiments, wherein the composition exhibits a viscosity of between 10 mPa*s and 70 mPa*s.

Additional aspects of the invention include the composition of any one of the above embodiments, wherein the composition includes a pharmaceutically acceptable excipient. In particular embodiments of the invention, the excipient is selected from the group consisting of polysorbate and propylene glycol.

Embodiments of the invention also include the composition of any of the above embodiments, wherein the aqueous solution containing the salt of a compound described herein, e.g., compound I, verapamil, gallopamil, or devapamil remains homogenous at room temperature. In certain cases, the aqueous solution containing the salt of a compound described herein, e.g., compound I, verapamil, gallopamil, or devapamil remains homogeneous at 10° C. for 4 days. In other cases, the aqueous solution containing the salt of compound I remains homogeneous at 2-5° C. for 7 days.

The present invention also includes a nasal delivery system containing a composition of any one of the above embodiments in a unit dosage form that contains no more than four single pump spray dosages. In alternative embodiments, the nasal delivery system contains the composition of any of the above embodiments in a unit dosage form that contains no more than two single pump spray dosages.

In other embodiments of the invention, the unit dosage form of the nasal delivery system is configured for administration of no more than 200 microliters of the composition to each nostril of a patient. In alternative forms of the invention, the unit dosage form of the nasal delivery system is configured for administration of no more than 150 microliters of the composition to each nostril of a patient.

Embodiments of the present invention additionally include a composition that contains the acetate salt of a compound described herein, e.g., compound I, verapamil, gallopamil, or devapamil. In alternative embodiments, the invention includes a composition that contains the methanesulfonate salt of a compound described herein, e.g., compound I, verapamil, gallopamil, or devapamil.

Alternative embodiments of the invention include a method for enhancing permeability through the nasal epithelium of an aqueous solution that contains the acetate salt or methanesulfonate salt of a compound described herein, e.g., compound I, verapamil, gallopamil, or devapamil formulated as a nasal spray solution, wherein the concentration of the salt of a compound described herein, e.g., compound I, verapamil, gallopamil, or devapamil is between 150 and 600 mg/mL and the pH of the solution is 4.5±1.5, the method including about 5 mM EDTA in the nasal spray solution.

Additional embodiments of the invention include a method of treating a disease selected from the group consisting of cardiac arrhythmia, stable angina, and migraine, the method including nasally administering to a patient in need thereof an aqueous composition that contains a pharmaceutically acceptable salt of a compound described herein, e.g., compound I, verapamil, gallopamil, or devapamil, wherein the compound is dissolved in the aqueous composition at a concentration of between 150 mg/mL and 600 mg/mL. In certain embodiments, the disease is cardiac arrhythmia. In other embodiments, the disease is stable angina. In alternative embodiments, the disease is migraine. In particular embodiments, the cardiac arrhythmia is PSVT, atrial fibrillation, or ventricular tachycardia.

Embodiments of the invention include the method of any of the above embodiments, wherein the compound reaches a therapeutically effective concentration in plasma of the patient within 3 to 5 minutes of administration to the patient.

Embodiments of the invention also include the method of any of the above embodiments that further includes administering between 150 microliters and 200 microliters of the aqueous composition to the patient.

Preferred embodiments of the invention include the method of any of the above embodiments, wherein the patient is a human.

Additional embodiments of the invention include the use of the composition of any one of the above embodiments in the manufacture of a medicament for the treatment of a disease selected from the group consisting of cardiac arrhythmia, stable angina, and migraine. In certain embodiments, the disease is cardiac arrhythmia. In other embodiments, the disease is stable angina. In alternative embodiments, the disease is migraine. In particular embodiments, the cardiac arrhythmia is PSVT, atrial fibrillation, or ventricular tachycardia.

The invention also includes a method of making a solution formulated for nasal administration to a patient, wherein the method includes the steps of
  a. adding a solution containing a first dissolved acid to the free base of the compound of any of the above embodiments to form a mixture;
  b. adding to the mixture a solution that contains ethylenediaminetetracetic acid;
  c. heating and mechanically stirring the resulting mixture until the compound has fully dispersed within the mixture;
  d. adjusting the pH of the mixture by adding a solution containing a second dissolved acid to the mixture; and
  e. diluting the mixture such that the final concentration of the compound in solution is at least 300 mg per 1 milliliter.

In certain embodiments of the invention, the first dissolved acid is selected from the group consisting of acetic acid and methanesulfonic acid.

In particular embodiments, the second dissolved acid is selected from the group consisting of acetic acid, sulfuric acid, and methanesulfonic acid.

In additional embodiments, the final pH of the solution is between about 4.0 and about 5.0. In preferred embodiments, the final pH of the solution is about 4.5.

Embodiments of the invention also include the above-described method, wherein the solution that contains the salt of a compound described herein, e.g., compound I, verapamil, gallopamil, or devapamil remains homogenous at 10° C. for 4 days. In alternative embodiments, the solution that contains the salt of a compound described herein, e.g., compound I, verapamil, gallopamil, or devapamil remains homogeneous at 2-5° C. for 7 days.

Definitions

The term "tachycardia" as used herein refers to a resting heart rate that is elevated relative to a normal state.

"Cardiac arrhythmia" as used herein refers to a condition characterized by abnormal heart rhythms that are irregular, too fast, too slow, or conducted via an abnormal electrical pathway through the heart. Cardiac arrhythmias include atrial fibrillation that is characterized by abnormally fast electrical discharge patterns that cause the atria to contract very rapidly thereby impairing efficient pumping of the blood into the ventricles. Cardiac arrhythmias also include PSVT that is characterized by a regular and fast heart rate originating in heart tissue above the ventricles. Cardiac arrhythmias also include ventricular tachycardia that is characterized by a rapid heartbeat that originates in the lower chambers of the heart.

The term "angina" as used herein refers to chest discomfort experienced due to ischemic heart disease. "Stable angina" is angina that is principally caused by arteriosclerosis.

The term "migraine" as used herein is a disease characterized by a recurrent headache that typically affects one side of the head and is often accompanied by nausea, vomiting, or sensitivity to light.

The term "excipient" is used herein to describe any ingredient other than an active compound (e.g., one having Formula I) described herein. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Additional excipients may include, without limitation, polysorbate, propylene glycol, hydroxypropyl β-cyclodextrin, triethylcitrate, benzalkonium chloride, and N-dodecyl-β-D-maltoside.

As used herein, a "chelating agent" is a molecule capable of forming at least two chemical bonds with a metal cation so as to form a complex.

As used herein, an "aminopolycarboxylic acid" is a molecule that includes at least one amine and at least two carboxylic acid functional groups. The carboxylic acids of an aminopolycarboxylic acid may be deprotonated and exist in anionic form as carboxylate groups. Examples of aminopolycarboxylic acids include, without limitation, iminodiacetic acid (IDA), nitrilotriacetic acid (NTA), pentetic acid (DTPA), ethylenediaminetetracetic acid (EDTA), ethylene glycol tetraacetic acid (EGTA), (1,2-bis(o-aminophenoxy) ethane-N,N,N',N'-tetraacetic acid) (BAPTA), 1,4,7,10-tetraazacyclododecane-1,4,7,10-tetraacetic acid (DOTA), and N—(N-(3-amino-3-carboxypropyl)-3-amino-3-carboxypropyl)azetidine-2-carboxylic acid (nicotianamine), among others.

As used herein, the term "nasal administration" means absorption of a compound or a pharmaceutically acceptable formulation of a compound by contacting the compound or formulation with the nasal epithelium. This can be achieved by spraying the compound or formulation into the nasal cavity. Desirably the compound is compound I, verapamil, gallopamil, or devapamil.

As used herein, a "pharmaceutically acceptable salt" or "pharmaceutically acceptable acid addition salt" of a basic pharmaceutically active compound is derived from the treatment of the compound with an organic acid or an inorganic acid. Exemplary pharmaceutically acceptable acid addition salts include those derived from treatment of the compound with acetic acid or methanesulfonic acid.

A "pharmaceutically acceptable carrier" As used herein, refers to a vehicle capable of suspending or dissolving the active compound, and having the properties of being non-toxic and non-inflammatory in a patient. Moreover, a pharmaceutically acceptable carrier may include a pharmaceutically acceptable additive, such as a preservative, antioxidant, fragrance, emulsifier, dye, or excipient known or used in the field of drug formulation and that does not significantly interfere with the therapeutic effectiveness of the biological activity of the active agent, and that is non-toxic to the patient.

The term "pharmaceutically acceptable formulation" As used herein, refers to a composition including a pharmaceutically acceptable carrier and an active compound, e.g., the compound of Formula I.

As used herein, the term "therapeutically effective amount" refers to an amount of an active compound that, when administered to a patient, reduces, eliminates, or prevents one or more symptoms of a cardiac arrhythmia (such as PSVT), stable angina, or migraine. Desirably, a therapeutically effective amount of a pharmaceutical formulation is an aqueous solution that contains a compound of the invention (e.g., a compound having Formula I) in a concentration range of about 150 mg/mL to about 600 mg/mL.

These definitions and others stated in The Merck Manual 16$^{th}$ edition 1992 (Chapter 25. pp 461-498; Chapter 25, pp 498-507; and Chapter 24, pp 413-429) and Goodman and Gilman's "The Pharmacological Basis of Therapeutics" 11$^{th}$ edition 2006 (Chapter 34, pp 899-908; Chapter 31, pp 823-824 and pp 830-832; and Chapter 32, pp 845-846) are herein incorporated by reference.

Other features and advantages of the invention will be apparent from the following Detailed Description and the Claims.

DETAILED DESCRIPTION

The present invention was derived from the surprising discovery that a previously characterized calcium channel blocker could be formulated as an acid addition salt derived from acetic acid or methanesulfonic acid so as to exhibit very high solubility in aqueous solution. The compounds of the instant invention include methyl 3-(2-((4-cyano-4-(3,4-dimethoxyphenyl)-5-methylhexyl)(methyl)amino)ethyl) benzoate, shown below in Formula I.

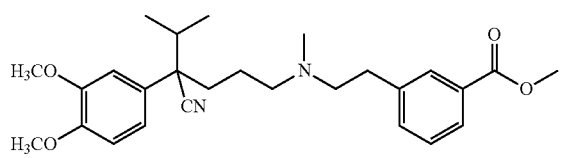
(I)

Additional compounds of the invention include other calcium channel blockers, such as verapamil, gallopamil, devapamil, and the particular compounds described herein.

Previously known formulations of calcium channel blockers, such as verapamil and diltiazem, do not provide immediate relief from cardiac arrhythmia, stable angina, or migraine. This is due in part to the pharmacokinetic profile of these drugs as formulated. As oral therapeutics, these compounds enter the body via gastrointestinal tract, where they are subject to acid-mediated or enzyme-catalyzed degradation and inactivation. These compounds slowly enter the bloodstream via absorption by the intestinal epithelium. To date, this route of administration has hindered the ability of these drugs to rapidly antagonize voltage-gated calcium channels at the site of deviant cardiac signaling that underlies cardiac arrhythmia, such as PSVT. As such, these drugs are commonly taken as a chronic preventative treatment regimen and are not used for the immediate relief of the symptoms of an episode of these diseases. Moreover, as calcium signaling also modulates normal cardiac muscle contractions, the ideal drug for treatment of an episode of cardiac arrhythmia, such as PSVT, will be absorbed quickly and subsequently metabolized and deactivated rapidly so as to mitigate off-target calcium channel inhibition. Indeed, common side effects of oral formulations of verapamil and diltiazem include attenuated cardiomyocyte contractility and depressed AV node conduction.

Water Soluble Aqueous Salts

Compound I and other calcium channel blockers, such as verapamil, gallopamil, and devapamil, as well as enantiomers and racemates of these compounds, may be dissolved in aqueous solution and formulated for nasal administration. Nasal administration offers an advantage over oral administration in that the pharmaceutically active agent can rapidly traverse the nasal epithelium and immediately enter the bloodstream. In this way, once a therapeutically effective amount of the active compound is in the bloodstream, the compound can disrupt aberrant cardiac signaling in the anomalous cardiac fibers and provide a patient with relief from an episode of cardiac arrhythmia, stable angina, or migraine once it has started. After persisting in the blood for a time sufficient to restore proper cardiomyocyte activity, the compound is metabolized and deactivated in rapid fashion, so as to prevent prolonged cardiac exposure and harmful side effects.

Despite the validated mechanisms of action of compound I, verapamil, gallopamil, and devapamil, nasal administration requires a high concentration of an active compound due to the volumetric limit imposed by the nasal cavity. Administration of nasal sprays is typically limited to approximately 150 to 200 µL, beyond which point the liquid solution begins to enter the throat. This, in turn, imposes a limit on the quantity of a pharmaceutically active agent that can be delivered to the epithelial lining of the nasal cavity.

In light of the prevalence of aromatic and saturated aliphatic moieties coupled with the lack of ionic or hydrogen bond-donating functionality, it was not expected that compound I, verapamil, gallopamil, or devapamil would be readily soluble in aqueous solution. Moreover, given that a solution of one of these compounds must be highly concentrated so as to enable the delivery of a therapeutically effective quantity of the drug within the volume limit imposed by the nasal cavity, prior to the present invention, it was unknown whether this could be achieved.

Surprisingly, concentrated aqueous solutions of compound I could be made by treating this compound with particular organic acids in order to produce acid addition salts. Methanesulfonic acid and acetic acid were capable of forming a salt solution with compound I with concentrations sufficient for nasal administration. For nasal administration, a desirable aqueous solution of compound I will exhibit a solubility of between approximately 150 mg/mL and 600 mg/mL (e.g., 150±25 mg/mL, 175±25 mg/mL, 200±25 mg/mL, 225±25 mg/mL, 250±25 mg/mL, 275±25 mg/mL, 300±25 mg/mL, 325±25 mg/mL, 350±25 mg/mL, 375±25 mg/mL, 400±25 mg/mL, 425±25 mg/mL, 450±25 mg/mL, 475±25 mg/mL, 500±25 mg/mL, 525±25 mg/mL, 550±25 mg/mL, 575±25 mg/mL, or 600±25 mg/mL). These concentrations correspond to a percentage of water of between 40% and 85% (w/v). Surprisingly, it was discovered that acetic acid and methanesulfonic acid were indeed capable of individually producing salts of compound I with high solubility in aqueous solution. The high solubility of the acetate and mesylate salts of compound I renders these salts uniquely suited for nasal administration, as the high concentrations of compound I attainable in these salt forms enable the delivery of a therapeutically effective amount of the compound within the volume limitation of the nasal cavity. Given the similarity in chemical structure between compound I and verapamil, gallopamil, and devapamil, as well as enantiomers and racemates thereof, these compounds are expected to be similarly soluble under the conditions described herein.

A common method of measuring the effectiveness of a therapeutic agent in terminating an episode of a cardiac arrhythmia, such as PSVT, is by analysis of an electrocardiogram (ECG) recorded from a patient experiencing such an episode. The pattern of an ECG describes the magnitude and timing of electrical signaling within the cardiac tissue, and patients suffering from an episode of PSVT typically exhibit a deviant ECG profile that is consistent with the aberrant signaling in the heart. One of the key features of healthy cardiac signaling is a temporal delay between the initiation of atrial and ventricular action potentials. A delay between signaling in the atria and ventricles is necessary for efficient pumping of blood. Signaling in the atria must proceed first, such that all blood in the atrial chambers is expelled into the ventricles before the ventricles contract. This delay is captured graphically on an ECG as the PR segment, which is the interval between the beginning of a P wave (corresponding to the onset of atrial depolarization) and the QRS complex (corresponding to the onset of ventricular depolarization). Patients suffering from an episode of PSVT typically experience a reduced delay due to aberrant cardiac signaling that causes the cardiomyocyte tissue to contract irregularly (Basta, et al., *Cardiol. Clinics*, 1997, 587-598). As such, these patients exhibit a reduced PR segment when monitored by ECG analysis.

It has been shown that an increase of at least 10% in the PR segment of an ECU recorded from a patient suffering from a cardiac arrhythmia correlates well with a termination of the PSVT episode. For instance, a therapeutic dose of verapamil administered intravenously to patients suffering from an episode of PSVT has been shown to induce a PR prolongation of at least 10%, which was correlated with an efficacy of 85-90% for terminating the PSVT episode (Reiter, et al., *Clin. Pharmacol. Ther.,* 1982, 711-720). It has also been shown that intravenous administration of tecadenoson is capable of inducing PSVT termination with an efficacy of approximately 86% (32 out of 37 patients treated experienced relief from an episode of PSVT). This result was correlated with an average PR prolongation of 8.5%. Collectively, these data indicate that a therapeutic agent capable of inducing a PR prolongation of at least about 10% would be expected to be effective in terminating an episode of PSVT in a patient. Experiments have been performed in which solutions of the invention containing the dissolved acetate salt of compound I were nasally administered to patients suffering from an episode of PSVT. The solutions that were administered to patients contained varying concentrations of the acetate salt of compound I. During the study, a solution containing a particular concentration of the acetate salt of compound I was administered to a patient experiencing an episode of PSVT, and the patient was monitored by electrocardiography throughout the duration of the experiment. Administration of solutions of the acetate salt of compound I containing 60 mg or greater of compound I were capable of inducing a median PR prolongation of greater than 10% in patients experiencing a PSVT episode. The results of these experiments demonstrate that a dosage containing 60 mg of compound I contains an amount of compound I that is therapeutically effective in terminating an episode of PSVT. Other preferable doses of a compound described herein, such as compound I, verapamil, gallopamil, or devapamil, include doses that range from 15 mg to 140 mg of the active compound (e.g., 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, etc.)

An aqueous solution containing the acetate or methanesulfonate salt of a compound described herein, such as compound I, verapamil, gallopamil, or devapamil, exhibit a particular viscosity range. In certain embodiments, the viscosity of such a solution can range from 10 mPa*s to 70 mPa*s (e.g., 10 mPa*s, 15 mPa*s, 20 mPa*s, 25 mPa*s, 30 mPa*s, 35 mPa*s, 40 mPa*s, 45 mPa*s, 50 mPa*s, 55 mPa*s, 60 mPa*s, 65 mPa*s, or 70 mPa*s). For example, a solution containing a salt of compound I at a concentration of 315 mg/mL exhibited a viscosity of between about 16.515 mPa*s to about 37.505 mPa*s. In another example, a solution containing a salt of compound I at a concentration of 360 mg/mL exhibited a viscosity of between about 25.645 mPa*S to about 63.105 mPa*s.

Permeation Enhancer

In order to exhibit an ideal pharmacokinetic profile, a pharmaceutically active compound or pharmaceutically acceptable salt thereof may be formulated with a material capable of enhancing the permeability of the active agent. In the formulation of the present invention, a compound described herein, such as compound I, verapamil, gallopamil, or devapamil, will ideally enter the bloodstream rapidly (e.g., within 3 to 5 minutes of administration to a patient).

In a preferred embodiment of the present invention, the permeation enhancer of the instant formulation is a chelating agent. More preferably, the chelating agent is capable of coordinating divalent calcium ions ($Ca^{2+}$). It has been shown that the epithelial cells of mucous membranes are held in close contact by the formation of tight junctions. The paracellular transport of a pharmaceutically active compound through the epithelium requires that the compound penetrate these intercellular junctions. Transcellular transport, the alternative to paracellular transport, requires that a compound penetrate the epithelium by traversing the apical and basolateral membranes, a process for which many molecules are not well-suited due to their large molecular volumes. Chelating agents render paracellular transport possible, however, by binding and sequestering intracellular calcium (Cassidy, et al., *J. Cell Biol.,* 1967, 32:685-698). Calcium is essential to the biogenesis of tight junctions between epithelial cells, and the reduction of intracellular calcium compromises the integrity of these junctions and enables certain molecules to penetrate the intercellular volume between neighboring cells.

Exemplary chelating agents capable of coordinating calcium ions include aminopolycarboxylic acids. These include, without limitation, iminodiacetic acid (IDA), nitrilotriacetic acid (NTA), pentetic acid (DTPA), ethylenediaminetetracetic acid (EDTA), ethylene glycol tetraacetic acid (EGTA), (1,2-bis(o-aminophenoxy)ethane-N,N,N',N'-tetraacetic acid) (BAPTA), 1,4,7,10-tetraazacyclododecane-1,4,7,10-tetraacetic acid (DOTA), and N—(N-(3-amino-3-carboxypropyl)-3-amino-3-carboxypropyl)azetidine-2-carboxylic acid (nicotianamine), among others. In a preferred embodiment, the chelating agent is EDTA.

Despite the use of chelating agents such as EDTA to increase the permeation capacity of drugs through epithelial tissue, it was nonetheless surprising that the use of EDTA in the instant formulation increased the permeation of compound I through the nasal epithelium. The nasal vestibule, which accounts for approximately 3-4% of the surface area of the nasal cavity, lacks tight junctions altogether and is thus not affected by calcium chelating agents. EDTA has been shown to modulate tight junction formation, but even when junctions are compromised, the intercellular pores in the nasal epithelium are particularly small. As such, it has been postulated that the nasal epithelium is not susceptible to permeability modulation by EDTA (Aungst, et al., *Pharma. Res.,* 1998, 5:305-308). Additionally, the ability of EDTA to increase permeation of a compound through the nasal epithelium is attenuated as the molecular weight of the compound increases (Nakanishi, et al., Chem. Pharm. Bull., 1984, 32:1628-1632).

pH Adjusting Agents

In certain embodiments of the invention, it is desirable to adjust the pH of the aqueous solution including a pharmaceutically acceptable salt of a compound described herein, such as compound I, verapamil, gallopamil, or devapamil. The pH of the formulation can be adjusted by treating the aqueous solution including a salt of one of these compounds with a solution including an acidic or a basic reagent. In preferred embodiments, the pH of the formulation is adjusted by titration of the aqueous solution with a solution including an acid. The pH of the formulation is desirably between 3.5 and 5.5, (e.g., 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, or 5.5), and is most desirably 4.5. The pH of the formulation can be adjusted by adding an aqueous solution containing an acid to the formulation so as to lower the pH to an ideal value. Exemplary acids that can be used to titrate an aqueous solution containing a salt of a compound described herein, such as compound I, verapamil, gallopamil, or devapamil, include, without limitation, acetic acid, sulfuric acid, and methanesulfonic acid. In preferred embodiments, the acid used to adjust the pH of the formulation is sulfuric acid or methanesulfonic acid.

Additional Excipients

Formulations of the instant invention may include other agents capable of increasing the permeation, solubility, stability, or efficacy of a compound described herein, such as compound I, verapamil, gallopamil, or devapamil. Pharmaceutically acceptable excipients may include antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Additional excipients may include, without limitation, polysorbate, propylene glycol, hydroxypropyl β-cyclodextrin, triethylcitrate, benzalkonium chloride, and N-dodecyl-β-D-maltoside.

The formulation of the present invention may optionally include a pharmaceutically acceptable carrier. Examples of a pharmaceutically acceptable carrier include, without limitation, a preservative, antioxidant, fragrance, emulsifier, dye, or excipient known or used in the field of drug formulation and that does not significantly interfere with the therapeutic effectiveness of the biological activity of the active agent, and that is non-toxic to the patient.

Nasal Delivery System

The present invention additionally provides a nasal delivery system for the administration of aqueous solutions of salts of a compound described herein, such as compound I, verapamil, gallopamil, or devapamil, to the nasal cavity of a patient suffering from cardiac arrhythmia, stable angina, or migraine. The nasal delivery system of the invention includes an aqueous solution of the acetate or methanesulfonate salt of a compound described herein, such as compound I, verapamil, gallopamil, or devapamil, in a unit dosage form. This solution may additionally contain other materials, including, without limitation, a permeation enhancer, pharmaceutically acceptable excipient, and/or a pH adjusting agent. The nasal delivery system includes the unit dosage form as a pump spray dosage. In this way, the nasal delivery system can be used to administer an aqueous solution containing the acetate or methanesulfonate salt of a compound described herein, such as compound I, verapamil, gallopamil, or devapamil, into the nasal cavity of a patient during an episode of cardiac arrhythmia, stable angina, or migraine. At the onset of an episode, a patient can easily self-administer this formulation containing one of these active compounds by inserting the applicator of the nasal delivery system into the nasal cavity and applying compressible pressure to the pump of the system. This will trigger the release of a spray including the aqueous solution of a salt of the active compound into the nasal cavity and onto the nasal epithelium.

The nasal delivery system is analogous to nasal delivery systems that are commercially available, such as those used to deliver such drugs as Imitrex® (sumatriptan), sold by GlaxoSmithKline (Brentford, UK) and Zomig® (zolmitriptan), sold by Impax Pharmaceuticals (Hayward, Calif., USA). These systems include a vial, a piston, a swirl chamber, and an actuator. Upon applying pressure to the actuator, the liquid is forced through the swirl chamber and released as a spray. These nasal delivery systems often include a pressure point mechanism to ensure that a reproducible pressure is applied to the system in order to achieve release of a consistent volume of spray (Rapoport, et al., *Headache*, 2006, 46:S192-S201). The nasal delivery system of the invention includes a unit dosage form that contains no more than four (e.g., one, two, three, or four single pump spray dosages. In alternative embodiments, the unit dosage form includes no more than two (e.g., one or two) single pump spray dosages. The unit dosage form can be configured for delivery of no more than 200 μL (e.g., 200 μL, 190 μL, 180 μL, 170 μL, 160 μL, 150 μL, 140 μL, 130 μL, 120 μL, 110 μL, or 100 μL) of the aqueous solution including a salt of a compound described herein, such as compound I, verapamil, gallopamil, or devapamil. In alternative embodiments, the unit dosage form is configured for delivery of no more than 150 μL (e.g., 150 μL, 140 μL, 130 μL, 120 μL, 110 μL, or 100 μL) of the aqueous solution including the acetate or methanesulfonate salt of a compound described herein, such as compound I, verapamil, gallopamil, or devapamil.

Methods of Formulation

The present invention additionally provides methods of making an aqueous solution including a salt of a compound described herein, such as compound I, verapamil, gallopamil, or devapamil. In certain embodiments of the invention, the free base of one of these compounds is treated with a solution including a first dissolved acid. The resulting mixture contains the acid addition salt including the protonated aminium form of the compound and the conjugate base of the first dissolved acid. Examples of the first dissolved acid that are suitable for formation of the salt of the active compound include acetic acid and methanesulfonic acid. EDTA may be added to this solution. The first dissolved acid may be added to the compound so as to form a salt containing the compound and between 0.5 and 1.5 molar equivalents of the acid. For example, the compound may be treated with acetic acid in order to form a salt containing the compound and between 0.5 and 1.5 molar equivalents of acetic acid relative to the compound. Alternatively, the compound may be treated with methanesulfonic acid in order to form a salt containing the compound and between 0.5 and 1.5 equivalents of methanesulfonic acid relative to the compound. In particular embodiments, the mixture containing the salt is heated and mechanically stirred until the compound has fully dispersed within the mixture. In additional embodiments, the pH of the mixture is then adjusted by adding a solution including second dissolved acid to this mixture. Examples of the second dissolved acid useful for adjusting the pH of the formulation include acetic acid, sulfuric acid, and methanesulfonic acid. In preferred embodiments, the second dissolved acid is sulfuric acid. In particular embodiments, the solution is subsequently diluted such that the final concentration of the compound in the mixture is at least 300 mg per 1 milliliter (e.g., 300 mg/mL, 310 mg/mL, 320 mg/mL, 330 mg/mL, 340 mg/mL, 350 mg/mL, 360 mg/mL, 370 mg/mL, 380 mg/mL, 390 mg/mL, 400 mg/mL, 410 mg/mL, 420 mg/mL, 430 mg/mL, 440 mg/mL, 450 mg/mL, 460 mg/mL, 470 mg/mL, 480 mg/mL, 490 mg/mL, 500 mg/mL, 510 mg/mL, 520 mg/mL, 530 mg/mL, 540 mg/mL, 550 mg/mL, 560 mg/mL, 570 mg/mL, 580 mg/mL, 590 mg/mL, 600 mg/mL, etc).

The acetate and methanesulfonate salts of a compound described herein, such as compound I, verapamil, gallopamil, or devapamil, can exhibit very high solubility in aqueous solution. An aqueous solution containing one of these salts can remain homogeneous for extended periods of time, even at high concentrations and at reduced temperatures. For example, highly concentrated solutions containing compound I and between 0.5 and 1.5 molar equivalents of acetic acid or methanesulfonic acid relative to the compound remain homogeneous at room temperature with no observable precipitation. In certain embodiments, these solutions remain homogeneous at 10° C. for at least 4 days, and in alternative embodiments these solutions are remain homogeneous at 2-5° C. for at least 7 days. For example, an aqueous solution containing 300 mg/mL of compound I, one molar equivalent of methanesulfonic acid 10 mM sodium acetate, and 5 mM disodium EDTA, adjusted to a pH of 4.5 with methanesulfonic acid, remains homogeneous at room temperature and at 2-5° C. without any observable precipitation. Moreover, this solution remains homogeneous even at 0° C. for at least 7 days. Additionally, an aqueous solution containing 400 mg/mL of compound I, one molar equivalent of methanesulfonic acid relative to compound I, 10 mM sodium acetate, and 5 mM disodium EDTA, adjusted to a pH of 4.5 with methanesulfonic acid also remains homogeneous at room temperature, 2-5° C. and remains homogeneous at 0° C. for at least 7 days. In another example, a solution containing 350 mg/mL of compound I and one molar equivalent of acetic acid relative to compound I, adjusted to a pH of 4.5 with 3.6 M sulfuric acid remains homogeneous at room temperature and also remains homogeneous at 10° C. for at least 3 days. Additionally, a solution containing over 500 mg/mL of compound I and one molar equivalent of acetic acid relative to compound I, adjusted to a pH of 4.5 with 3.6 M sulfuric acid remains homogeneous at room temperature.

In order that this invention be more fully understood, the following examples are set forth. These examples are for the purpose of illustration only and are not to be construed as limiting the scope of the invention in any way.

EXAMPLES

Example 1: Synthesis methyl 3-(2-((4-cyano-4-(3,4-dimethoxyphenyl)-5-methylhexyl)(methyl)amino)ethyl)benzoate Part I: Synthesis of 5-Bromo-2-(3,4-dimethoxyphenyl)-2-isopropylpentanenitrile

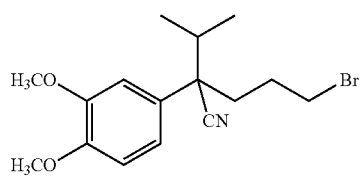

(II)

Method A, Step 1:

To a solution of 9.99 g (56.4 mmol) of (3,4-Dimethoxyphenyl)acetonitrile in 141 mL of tetrahydrofuran (THF) at −30° C., was slowly added 56.4 mL (56.4 mmol) of sodium bis(trimethylsilyl)amide (NaHMDS, 1.0 M in THF). The mixture was stirred at −30° C. for 10 minutes and 10.6 mL (113.0 mmol) of 2-bromopropane was added. The mixture was heated to reflux for 2 hours (h) then left at 22° C. for about 16 h. A saturated aqueous solution of NH$_4$Cl was added and the mixture was extracted with ethyl acetate. The organic layer was washed with brine, dried (Na$_2$SO$_4$), filtered and evaporated. The residue was purified by flash chromatography on silica gel eluting first with hexane and then gradually increasing to 15% ethyl acetate/hexane to give 2-(3,4-dimethoxyphenyl)-3-methylbutanenitrile as an oil.

Method A, Step 2:

To a solution of 11.21 g (51.1 mmol) of 2-(3,4-dimethoxyphenyl)-3-methylbutanenitrile in 126 mL of tetrahydrofuran (THF) at −30° C., was slowly added 46.0 mL (46.0 mmol) of sodium bis(trimethylsilyl)amide (NaHMDS, 1.0 M in THF). The mixture was stirred at −30° C. for 10 minutes and 9.40 mL (256 mmol) of 1,3-dibromopropane was added dropwise. The mixture was warmed to 22° C. and stirred for about 16 h. A saturated aqueous solution of NH$_4$Cl was then added and the mixture was extracted with ethyl acetate. The organic layer was washed with brine, dried (Na$_2$SO$_4$), filtered and evaporated. The residue was purified by flash chromatography on silica gel eluting first with hexane and then gradually increasing to 15% ethyl acetate/hexane to give 5-bromo-2-(3,4-dimethoxyphenyl)-2-isopropylpentanenitrile as an oil.

Part II: Synthesis of methyl 3-(2-(methylamino)ethyl)benzoate

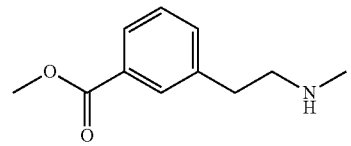

(III)

To a solution of 5.71 g (24.9 mmol) of methyl 3-bromomethylbenzoate in 36 mL of methanol was added 2.11 g (32.4 mmol) of potassium cyanide. The mixture was refluxed for about 16 h, cooled to 22° C. and filtered. The filtrate was evaporated and the residue was purified by flash chromatography on silica gel, eluting first with hexane and then gradually increasing to 15% ethyl acetate/hexane to give methyl 3-(cyanomethyl)benzoate.

To a solution of 1.31 g (7.48 mmol) of methyl 3-(cyanomethyl)benzoate in 31 mL of THF stirred at −10° C. was slowly added 710 mg (18.7 mmol) of sodium borohydride followed by 1.44 mL (18.7 mmol) of trifluoroacetic acid. The mixture was warmed to 22° C. and stirred for about 16 h. About 100 mL of water was carefully added to the mixture (gas evolution). The mixture was extracted with ethyl acetate (5×50 mL). The organic phase was washed with brine, dried (Na$_2$SO$_4$), filtered and evaporated to give methyl 3-(2-aminoethyl)benzoate which was used in the next step without purification.

Method B:

To 5.12 g (28.6 mmol) of methyl 3-(2-aminoethyl)benzoate in 71 mL tetrahydrofuran (THF) was added 7.48 g (34.3 mmol) of BOC$_2$O. The mixture was stirred for about 16 h at 22° C. and 100 mL of water was added. The mixture was extracted with ethyl acetate (2×100 mL) and the organic phase was washed with brine, dried (Na$_2$SO$_4$) and evaporated. The residue was purified by flash chromatography on silica gel, eluting first with hexane and then gradually increasing to 20% ethyl acetate/hexane to give methyl 3-(2-(tert-butoxycarbonylamino)ethyl)benzoate which was further converted to III by Method C (described below).

Method C, Step 1:

To a solution of methyl 3-(2-(tert-butoxycarbonylamino) ethyl)benzoate in dry THF under a nitrogen atmosphere was added dropwise NaHMDS (1.0 M in THF) at 0° C. After stirring for 10 min, dimethyl sulfate was added and the reaction was warmed to 22° C. and stirred for about 16 h. The reaction was quenched by adding 25 mL of saturated NaHCO$_3$ and the mixture was extracted with DCM (2×25 mL). The combined organic extracts were dried (Na$_2$SO$_4$) and evaporated and the residue was purified by flash chromatography on silica gel, eluting first with hexane and then gradually increasing to 10% ethyl acetate/hexane to give methyl 3-(2-(tert-butoxycarbonyl(methyl)amino) ethyl)benzoate.

Method C, Step 2:

To a solution of methyl 3-(2-(tert-butoxycarbonyl (methyl)amino) ethyl)benzoate in DCM at 0° C. was added trifluoroacetic acid (TFA). The reaction was warmed to 22° C., stirred for 3 h and the solvents were then evaporated. The residue was partitioned between 100 mL of ethyl acetate and 100 mL of 1 N NaOH which had been saturated with NaCl. The aqueous layer was back-extracted with ethyl acetate (6×50 mL) and the combined organics were dried (Na$_2$SO$_4$) and evaporated to give 2c as a colorless oil.

Part III: Reaction of Compound II with Compound III Produced Compound I

Analysis of the product by mass spectrometry revealed a peak with a mass-to-charge ratio (m/z) of 453, corresponding to the M+H molecular ion of compound I.

Example 2: Concentrated Solution of Acetate Salt of Compound I

A concentrated aqueous solution of the acetate salt of compound I is formed according to the following protocol:

An aqueous solution of 7.5 M sulfuric acid is first made by diluting concentrated sulfuric acid in water and manually mixing in a sealed bottle, periodically venting the pressure by releasing the bottle cap. Separately, 175±1.0 g of compound I is dispensed from a pre-heated container into a glass bottle and maintained at a temperature of 50±2° C. in a water bath. Next, 96.7±0.2 mL of a 4.0 M acetic acid solution is added to compound I, followed by 83.3 mL±0.2 mL of a 31.8 mM solution of EDTA. The mixture containing the (−) enantiomer (S-enantiomer) of compound I is maintained at 50±2° C. and stirred using a magnetic stir bar during both additions. Heating and stirring is continued until the compound appears to be fully dispersed throughout the mixture.

Upon complete dispersion of compound I, the solution of 7.5 M sulfuric acid is added drop-wise to the compound I mixture until a pH of 5.0±0.1 is reached. At this point, heating is discontinued and the mixture continues to stir. The mixture is then allowed to cool to within 2° C. of ambient temperature. A solution of 0.9 M sulfuric acid is then added drop-wise to the mixture until a pH of 4.5±0.1 is reached. The mixture containing compound I is then diluted to 90% of the final target volume by the addition of water to the mixture, and the pH is monitored after this dilution. If necessary, the pH is lowered back to 4.5±0.1 by drop-wise addition of 0.9 M sulfuric acid. The mixture is then diluted to the final target volume by the addition of water.

This protocol readily can be adapted to provide a concentrated solution of the methanesulfonate salt of compound I.

Example 3: Nasal Administration of Compound I

A patient experiencing an episode of PSVT can use a nasal delivery system containing the acetate or methanesulfonate salt of compound I in order to nasally self-administer a therapeutically effective amount of compound I and alleviate the symptoms of this episode. At the onset of an episode of PSVT, a patient can hold the nasal delivery system up to the nose, such that the applicator of the system is inserted into the nasal cavity. The nasal delivery system is typically held between the second and third fingers, and the patient's thumb is placed on the actuator. This process is similar to the use of commercially available nasal delivery systems such as those used to deliver such drugs as Imitrex® (sumatriptan), sold by GlaxoSmithKline (Brentford, UK) and Zomig® (zolmitriptan), sold by Impax Pharmaceuticals (Hayward, Calif., USA). The patient can then apply pressure to the actuator, which forces the liquid solution containing the dissolved acetate or methanesulfonate salt of compound I through a swirl chamber, causing the solution to be released from the tip of the applicator as a spray. The solution may be administered as one, two, three, or four single pump spray dosages in order to deliver 60 mg or more of compound I to the nasal epithelium.

The spray administered as described delivers the solution containing the acetate or methanesulfonate salt of compound I to the nasal epithelium, allowing compound I to penetrate the epithelium and rapidly enter the bloodstream. The acetate or methanesulfonate salt of compound I administered in this way reaches a maximum concentration in plasma within 3 to 5 minutes after administration to the patient, and minimal concentrations of the compound in plasma are observed within 50 to 60 minutes of administration. In this manner, the patient experiences relief from an episode of PSVT very soon after administration, and because of the ideal pharmacokinetic profile of compound I, the drug does not persist in the bloodstream long enough to induce adverse side effects.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All references, patents, patent application publications, and patent applications cited herein are hereby incorporated by reference to the same extent as if each of these references, patents, patent application publications, and patent applications were separately incorporated by reference herein.

What is claimed is:

1. An aqueous composition formulated for nasal administration comprising a pharmaceutically acceptable salt or free base of compound I:

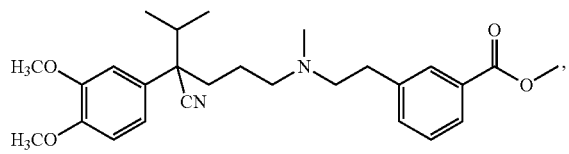 [SMILES: COC(=O)c1cccc(CCN(C)CCCC(C#N)(c2ccc(OC)c(OC)c2)C(C)C)c1]

or a racemate or enantiomer thereof, wherein compound I, or the racemate or enantiomer thereof, is dissolved in the aqueous composition at a concentration of between 150 mg/mL and 600 mg/mL.

2. The aqueous composition of claim 1, wherein the aqueous composition comprises the S-enantiomer of compound I.

3. The aqueous composition of claim 1, wherein the concentration is 350 mg/mL±25 mg/mL.

4. The aqueous composition of claim 1, wherein the aqueous composition comprises from 40% to 85% (w/v) water.

5. The aqueous composition of claim 1, wherein the aqueous composition has a pH of 4.5±1.5.

6. The aqueous composition of claim 1, wherein the aqueous composition comprises compound I, or the racemate or enantiomer thereof, and between 0.5 and 1.5 molar equivalents of acetic acid relative to the compound.

7. The aqueous composition of claim 1, wherein the aqueous composition comprises compound I, or the racemate or enantiomer thereof, and between 0.5 and 1.5 molar equivalents of methanesulfonic acid relative to the compound.

8. The aqueous composition of claim 1, wherein the aqueous composition further comprises a chelating agent.

9. The aqueous composition of claim 1, wherein the aqueous composition further comprises EDTA.

10. The aqueous composition of claim 1, wherein the aqueous composition further comprises a pharmaceutically acceptable excipient.

11. The aqueous composition of claim 1, wherein the aqueous composition is a homogeneous composition at room temperature.

12. A nasal delivery system comprising an aqueous composition of claim 1 in a unit dosage form comprising no more than four single pump spray dosages.

13. A nasal delivery system comprising an aqueous composition of claim 1 in a unit dosage form comprising no more than two single pump spray dosages.

14. The nasal delivery system of claim 13, wherein the unit dosage form is configured for administration of no more than 200 microliters of the composition to each nostril of a patient.

15. A method of treating a disease selected from the group consisting of cardiac arrhythmia, stable angina, and migraine, said method comprising nasally administering to a patient in need thereof an aqueous composition comprising a pharmaceutically acceptable salt of compound I:

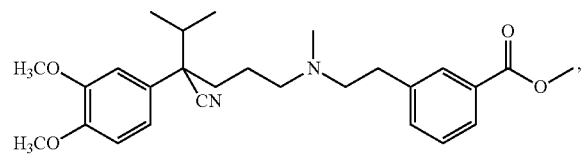

or a racemate or enantiomer thereof, wherein compound I, or the racemate or enantiomer thereof, is dissolved in the aqueous composition at a concentration of between 150 mg/mL and 600 mg/mL.

16. The method of claim 15, wherein said cardiac arrhythmia is PSVT, atrial fibrillation, or ventricular tachycardia.

17. The method of claim 15, the method comprising administering between 150 microliters and 200 microliters of the aqueous composition to the patient.

18. A method of making a solution formulated for nasal administration to a patient, the method comprising the steps of
  a) adding a solution comprising a first dissolved acid to the free base of a compound of claim 1 to form a mixture;
  b) adding to the mixture a solution comprising ethylenediaminetetracetic acid;
  c) heating and mechanically stirring the resulting mixture until the compound has fully dispersed within the mixture;
  d) adjusting the pH of the mixture to be between 3.5 and 5.5 by adding a solution comprising a second dissolved acid to the mixture; and
  e) diluting the mixture such that the final concentration of the compound in solution is at least 300 mg per 1 milliliter.

19. The method of claim 18, wherein the first dissolved acid is selected from the group consisting of acetic acid and methanesulfonic acid.

20. The method of claim 18, wherein the second dissolved acid is selected from the group consisting of acetic acid, sulfuric acid, and methanesulfonic acid.

21. The aqueous composition of claim 1, wherein the pharmaceutically acceptable salt is the acetate salt of the S-enantiomer of compound I.

22. An aqueous composition formulated for nasal administration comprising the acetate salt of the S-enantiomer of compound I:

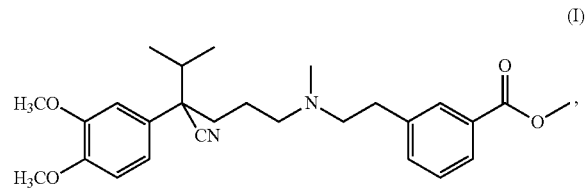 [SMILES: COC(=O)c1cccc(CCN(C)CCCC(C#N)(c2ccc(OC)c(OC)c2)C(C)C)c1]

dissolved in the aqueous composition at a concentration of 350 mg/mL±25 mg/mL.

23. The aqueous composition of claim 22, wherein the S-enantiomer of compound I is dissolved in the aqueous composition at a concentration of 350 mg/mL.

24. The aqueous composition of claim 22, wherein the aqueous composition has a pH of 4.5±0.1.

25. The aqueous composition of claim 22, wherein the aqueous composition further comprises between 0.5 and 1.5 molar equivalents of acetic acid relative to the compound.

26. The aqueous composition of claim 22, wherein the aqueous composition further comprises sulfuric acid.

27. The aqueous composition of claim 22, wherein the aqueous composition further comprises EDTA.

28. The nasal delivery system of claim 13, wherein the aqueous composition comprises the S-enantiomer of compound I.

29. The nasal delivery system of claim 13, wherein each of the two single pump spray doses comprises 35 mg of the S-enantiomer of compound I.

30. The nasal delivery system of claim 13, wherein each of the two single pump spray doses comprises 100 microliters of the aqueous composition.

31. The method of claim 16, wherein said cardiac arrhythmia is PSVT.

32. A method of treating PSVT, said method comprising nasally administering to a patient in need thereof an aqueous composition comprising the acetate salt of the S-enantiomer of compound I:

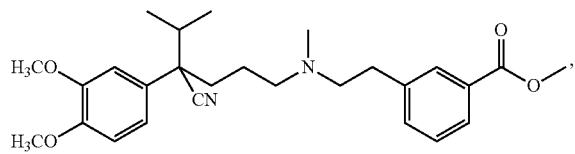 [SMILES: COC(=O)c1cccc(CCN(C)CCCC(C#N)(c2ccc(OC)c(OC)c2)C(C)C)c1]

wherein the compound is dissolved in the aqueous composition at a concentration of 350 mg/mL±25 mg/mL.

33. The method of claim 32, wherein 70 mg of the acetate salt of the S-enantiomer of compound I is administered to the patient.

34. The method of claim 32, wherein the S-enantiomer of compound I is dissolved in the aqueous composition at a concentration of 350 mg/mL.

35. The method of claim 18, wherein the final concentration of the compound in solution is 350 mg/mL±25 mg/mL.

36. The method of claim 18, wherein the first dissolved acid is acetic acid and the second dissolved acid is sulfuric acid.

37. The method of claim 18, wherein, in step d), the pH is adjusted to be 4.5±0.1.

38. A method of making a solution formulated for nasal administration to a patient, the method comprising the steps of
a) adding a solution comprising acidic acid to the free base of the S-enantiomer of compound I:

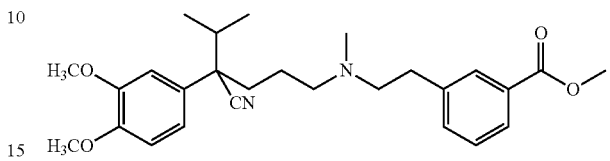

to form a mixture;
b) adding to the mixture a solution comprising ethylenediaminetetracetic acid;
c) heating and mechanically stirring the resulting mixture until the S-enantiomer of compound I has fully dispersed within the mixture;
d) adjusting the pH of the mixture to be 4.5±0.1 by adding a solution comprising sulfuric acid to the mixture; and
e) diluting the mixture such that the final concentration of the S-enantiomer of compound I in solution is 350 mg/mL±25 mg/mL.

39. The method of claim 38, wherein the final concentration of the S-enantiomer of compound I in solution is 350 mg/mL.

* * * * *

UNITED STATES PATENT AND TRADEMARK OFFICE
CERTIFICATE OF CORRECTION

PATENT NO. : 10,117,848 B2
APPLICATION NO. : 15/566122
DATED : November 6, 2018
INVENTOR(S) : Martin P. Maguire It is certified that error appears in the above-identified patent and that said Letters Patent is hereby corrected as shown below:

In the Specification

Column 7, Line 10 should read:

-- 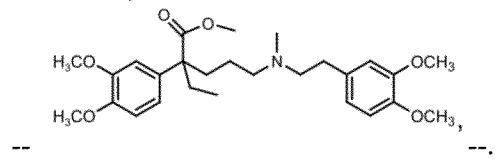 --.

Signed and Sealed this
First Day of September, 2020

Andrei Iancu
*Director of the United States Patent and Trademark Office*